United States Patent [19]

Siczek

[11] Patent Number: 4,618,133
[45] Date of Patent: Oct. 21, 1986

[54] TABLE POSITIONER FOR RADIOGRAPHIC DEVICE

[75] Inventor: Bernard W. Siczek, Boulder, Colo.

[73] Assignee: Fischer Imaging Corporation, Denver, Colo.

[21] Appl. No.: 687,437

[22] Filed: Dec. 28, 1984

[51] Int. Cl.$^4$ ............................................. A61G 13/00
[52] U.S. Cl. .................................... 269/323; 378/209
[58] Field of Search .............. 269/323; 378/209; 5/62; 108/1, 7, 5

[56] References Cited

U.S. PATENT DOCUMENTS

| | | | |
|---|---|---|---|
| 2,680,046 | 6/1954 | Stava | 378/209 X |
| 2,692,173 | 10/1954 | Lowitzsch | 378/209 X |
| 3,131,301 | 4/1964 | Barrett et al. | 269/323 |
| 3,525,308 | 8/1970 | Koopmans | 269/323 X |
| 3,532,882 | 10/1970 | Craig et al. | 269/323 |
| 3,822,875 | 7/1974 | Schmedemann | 378/209 X |

FOREIGN PATENT DOCUMENTS

2932755  3/1981  Fed. Rep. of Germany ...... 378/209

*Primary Examiner*—Frederick R. Schmidt
*Assistant Examiner*—Steven P. Schad
*Attorney, Agent, or Firm*—Robert E. Harris

[57] ABSTRACT

A table positioner is disclosed for use with radiographic equipment to cause smooth translating and continuous angular movement of the table in reciprocal directions from a lengthwise horizontal position to lengthwise vertical positions. When in a lengthwise horizontal position, the positioner causes the top of the table to have a sufficiently low vertical height above floor level to enhance utilization of the radiographic equipment for imaging of a patient on the table, and yet still allows lengthwise angular movement of the table from this low horizontal positioning to full vertical positioning with the then lower end of the table being maintained in a position close to floor level but precluding floor contact during any portion of table movement. Lengthwise angular movement of the table is effected through use of a pair of gear racks mounted on a moveable frame with the gear racks being curved in opposite directions with respect to one another and engageable with drive gears one of which is mounted on a pivotable yoke mounted on the frame and operating in conjunction with the gear racks and drive gears to effect the smooth translating and continuous motion of the frame.

17 Claims, 13 Drawing Figures

Fig_1

Fig_2

Fig_3

Fig_4

Fig_6

Fig_9

Fig_11

Fig_10

Fig_12

Fig_13

TABLE POSITIONER FOR RADIOGRAPHIC DEVICE

FIELD OF THE INVENTION

This invention relates to a table positioner for use with radiographic equipment, and, more particularly, relates to a table positioner for effecting smooth translating and continuous lengthwise angular movement of such a table.

BACKGROUND OF THE INVENTION

The use of a table for positioning a patient in order to effect treatment and/or a diagnostic examination is well known, and such tables have heretofore been controlled utilizing various devices for effecting needed movement, including the use of electric motors and the like.

Improvements in positioners for such tables are, however, deemed to be still useful and/or needed for at least some applications. In particular, now known positioners for some such tables have not been able to impart lengthwise angular movement in a full 90° from horizontal, have lacked the ability to impart a smooth translating and/or continuous motion, have required that the table have an undue height above floor level for effective use, when horizontally positioned, have required a plurality of pivot points and/or extension devices, and/or have failed to provide adequate imaging coverage of a patient on the table.

SUMMARY OF THE INVENTION

This invention provides an improved table positioning system for use with radiographic equipment and which allows the table to be lengthwise angularly displaced up to 90° in either direction from a horizontal position, with such movement being effected by a smooth translating and continuous motion that allows the table to be positioned low, relative to floor level, when in a horizontal position, and yet be lengthwise angularly moved from the horizontal position with the then lower end of the table being maintained near floor level but without making floor contact during such movement of the table.

It is therefore an object of this invention to provide an improved table positioning system.

It is another object of this invention to provide an improved table positioning system useful in conjunction with radiographic equipment.

It is still another object of this invention to provide an improved table positioning system having smooth translating and continuous motion.

It is still another object of this invention to provide an improved table positioning system for maintaining the table low, with respect to floor level, when in a horizontal position and yet enables the table to be lengthwise angularly moved in reciprocal directions up to a full vertical position with the then lower end of the table being maintained close to but avoiding floor contact during said movement of the table.

It is yet another obejct of this invention to provide an improved table positioning system which provides adequate imaging coverage of a patient on the table.

With these and other objects in view, which will become apparent to one skilled in the art as the description proceeds, this invention resides in the novel construction, combination, and arrangement of parts substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figure 1:
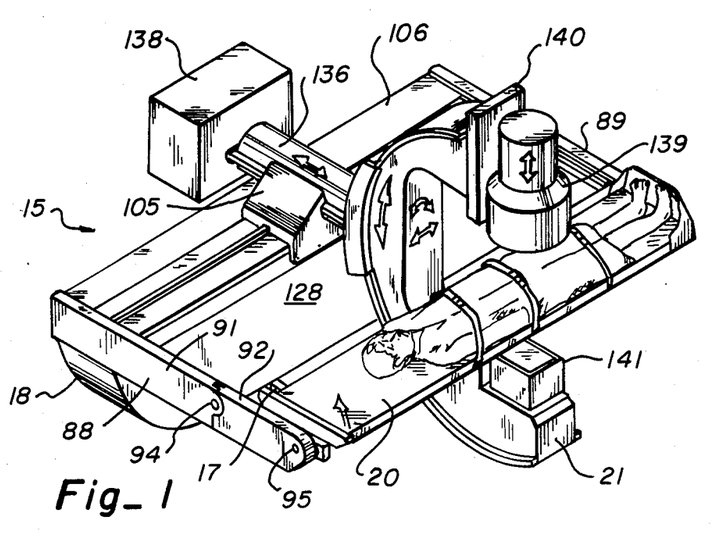
FIG. 1 is an isomeric view of an imaging apparatus having the table positioning system of this invention incorporated therein.
Figure 2:
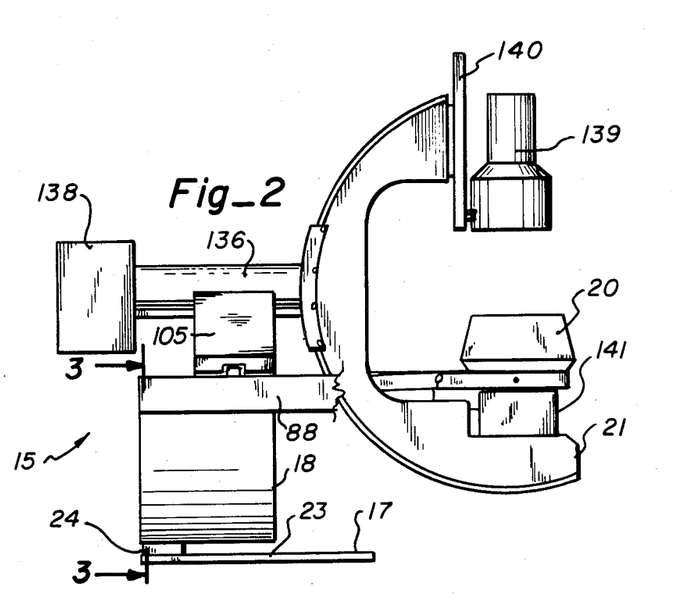
FIG. 2 is an end view of the imaging apparatus shown in FIG. 1.

Imaging device 15 having the table positioning system of this invention incorporated therein is best shown by the isomeric drawing of FIG. 1, augmented by the end view of FIG. 2. As shown, imaging device 15 includes a base unit 17 having mounted thereon a lengthwise angularly moveable frame 18, which frame has a table 20 and a C-arm 21 moveably mounted thereon.

Figure 3:
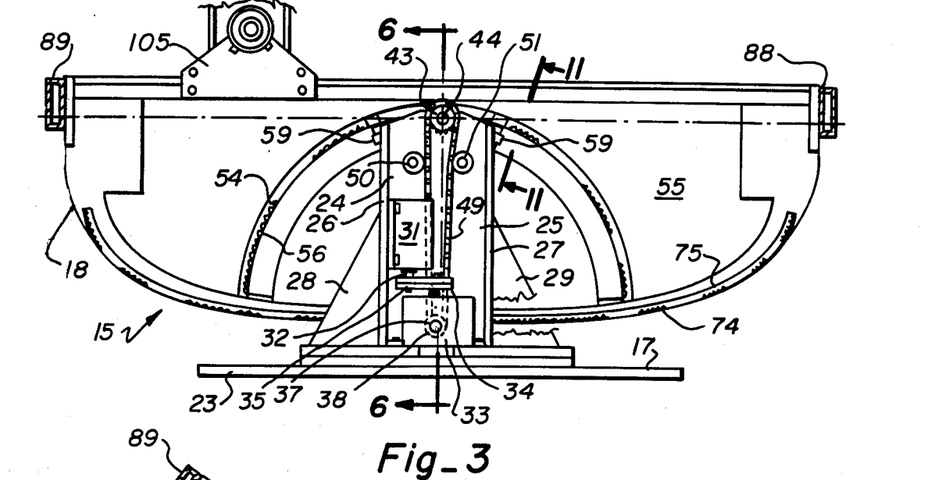
FIG. 3 is a rear section view taken through lines 3—3 of FIG. 2 and illustrating the frame in a horizontal position relative to floor level.
Figure 4:
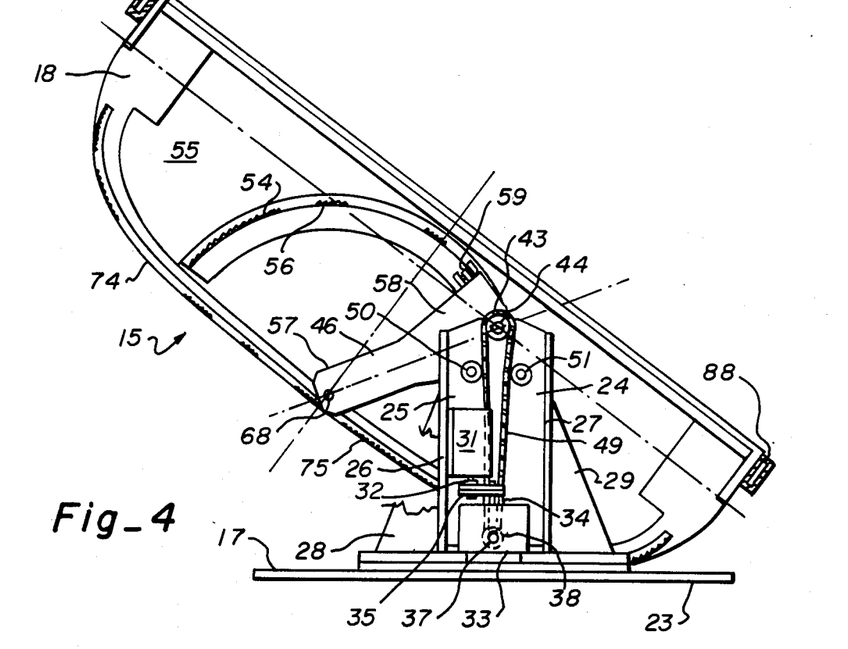
FIG. 4 is a view similar to that of FIG. 3, but showing the frame lengthwise angularly oriented at an angle of approximately 35° from horizontal.
Figures 5, 7, 8:
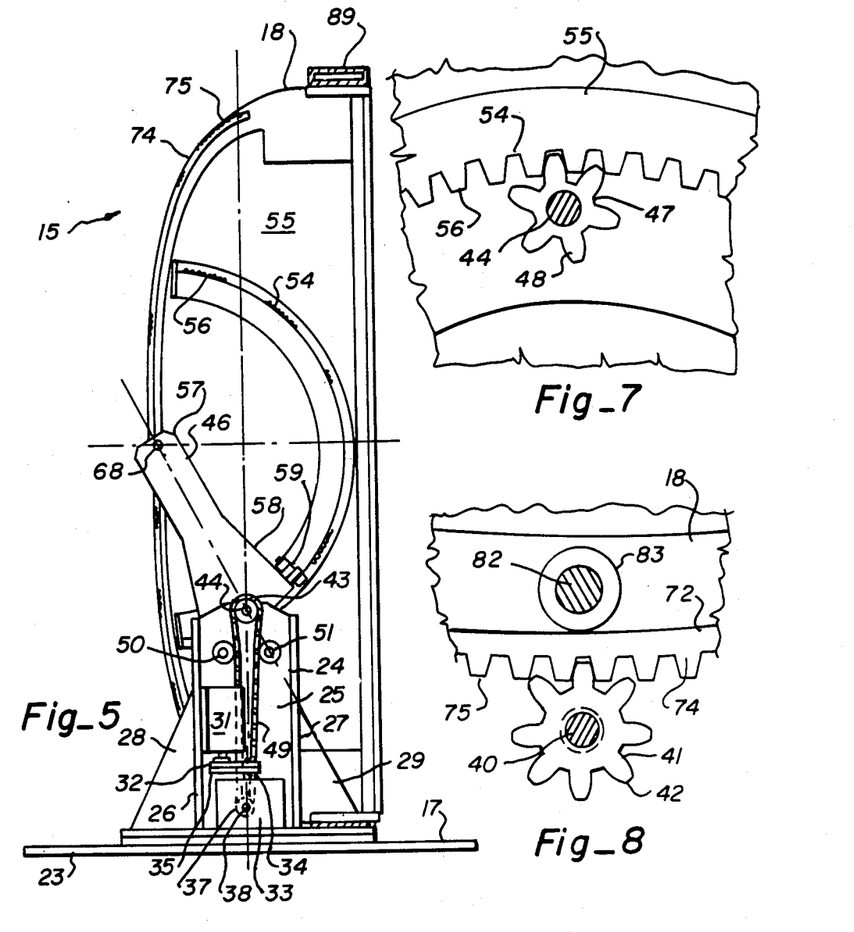
FIG. 5 is a view similar to that of FIGS. 3 and 4, but showing the frame lengthwise angularly oriented at a full 90° from horizontal.
FIG. 7 is a section view taken through lines 7—7 of FIG. 6.
FIG. 8 is a section view taken through lines 8—8 of FIG. 6.

Base 17 includes a horizontally extending floor engaging section 23 (which can include a plurality of stacked plates, if desired, as indicated in FIGS. 3 through 5) and a vertically extending support section 24, which section extends upwardly from section 23. Support section 24, as shown best in FIGS. 3 through 5, includes a mounting plate 25 having support plates 26 and 27 connected at the outer edge portions thereof and extending rearwardly therefrom. Support section 24 also includes triangularly shaped support plates 28 and 29 connected with and extending outwardly from support plates 26 and 27, respectively.

Figure 10:
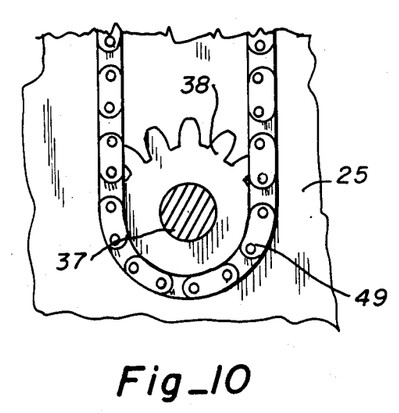
FIG. 10 is a section view taken through lines 10—10 of FIG. 6.

Electric motor 31 is mounted on support plate 26 and has a dual belt motor shaft pulley 32 thereon that is rotated by the motor. Reduction box 33 is mounted at the top of floor engaging section 23 and has a dual belt pulley 34 thereon with pulleys 32 and 34 having dual belts 35 extending therearound. In addition, reduction box 33 has an output drive shaft 37 which is connected to lower chain sprocket 38 (see FIGS. 6 and 10) and to flexible coupling 39 (see FIG. 6) connected to shaft 40, which shaft has mounted thereon lower frame drive gear 41, which gear has gear teeth 42 thereon.

Figures 9, 11:
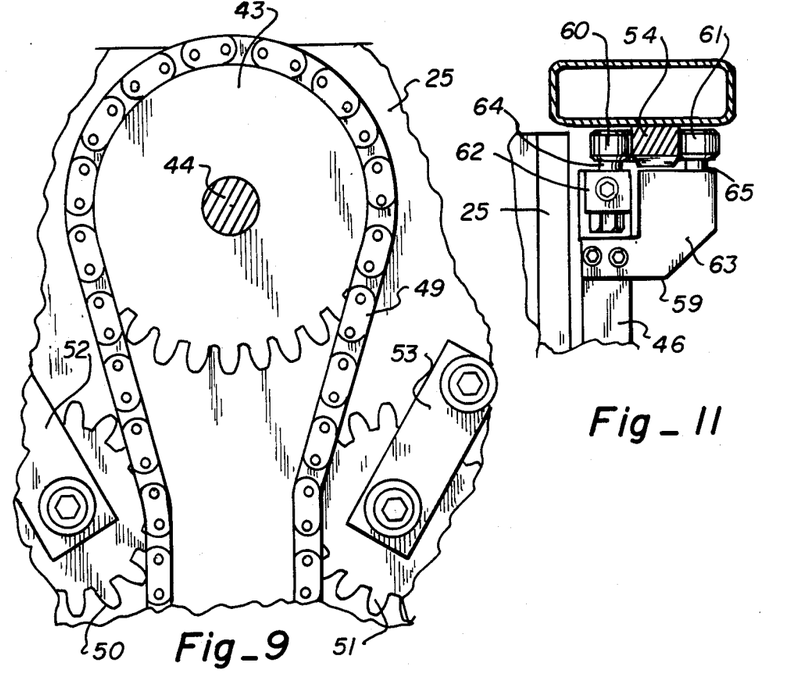
FIG. 9 is a section view taken through lines 9—9 of FIG. 6.
FIG. 11 is a section view taken through lines 11—11 of FIG. 3.

Upper chain sprocket 43 is mounted on shaft 44, which shaft is freely rotatable within bearing 45 which extends through mounting plate 25 and is mounted on yoke 46. The opposite end of shaft 44 has mounted thereon an upper frame drive gear 47, which gear has teeth 48 thereon. Chain 49 extends around lower and upper sprockets 38 and 43, and is tensioned by gears 50 and 51, which gears are mounted on plate 25 by straps 52 and 53, respectively, as shown in FIG. 9.

Frame 18 has a half-moon shaped radial gear rack, or cog, 54 formed therein at a semi-cylindrical wall portion of rear wall 55. Gear rack 54 has inwardly facing gear teeth 56 engageable with the teeth 48 of upper frame drive gear 47 (as shown best in FIG. 7) so that driving rotation of gear drive 47 causes movement of the frame. As shown best in FIGS. 3 through 5, gear rack 54 extends from near the bottom of frame 18 arcuately upwardly and inwardly to the central top portion of the frame and then arcuately downwardly and outwardly to near the bottom of the frame.

Plate-like yoke 46 has a lower portion 57 which widthwise spreads outwardly at an upper portion 58. Bearing 45 is centrally mounted at the upper portion 58 of yoke 46 (as brought out hereinabove, shaft 44 is received through bearing 45). Guide members 59 are provided at each of the upper outer edges of the upper portion 58 of yoke 46. As shown best in FIG. 11, each guide member 59 includes a pair of rollers 60 and 61 positioned at the opposite sides of gear rack 54 by means of mounts 62 and 63, respectively, which mounts have pins 64 and 65 upon which rollers 60 and 61 are mounted for free rotation.

The lower center portion 57 of yoke 46 is pivotally mounted to L-shaped wall section 67 of frame 18 by means of pivot pin 68 which extends rearwardly from depending wall 69 of wall section 67.

Wall section 67 is mounted on the inner side wall 71 of wall 55 of frame 18, and inner wall 71 has an inwardly extending wall section 72 below wall section 67. Wall section 72 has gear rack, or cog, 74 mounted thereon with the teeth 75 of gear rack 74 facing outwardly from the bottom wall. As shown best in FIGS. 3 through 5, gear rack 74 follows the outline of the lower portion of frame 18 and has a slight curvature at the center portion that rapidly increases in curvature at the outer edges. This curvature is selected as needed to achieve the desired ends as brought out more fully herein- after.

Figure 6:
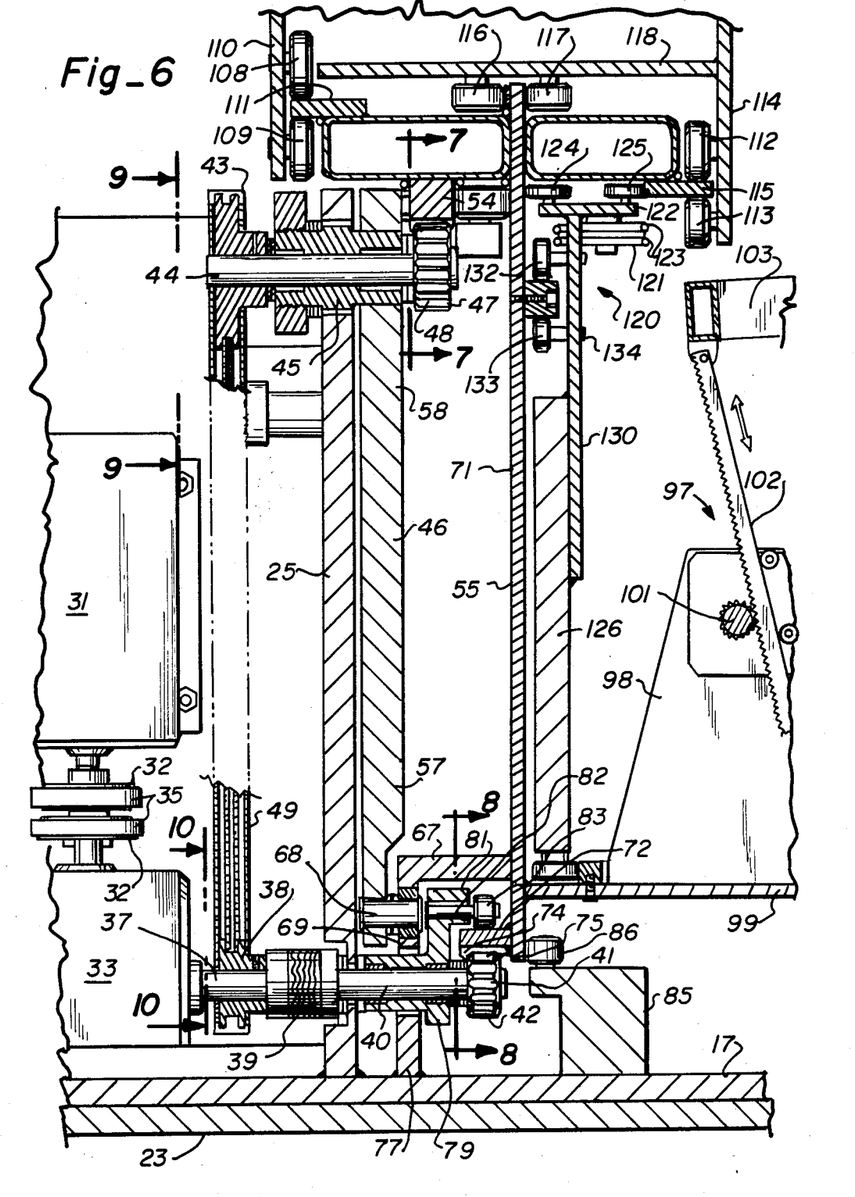
FIG. 6 is a side section view taken through lines 6—6 of FIG. 3.

As best shown in FIG. 8, the teeth 42 of lower gear rack drive 41 engage the teeth 75 of gear rack 74 to impart driving motion to frame 18. As best shown in FIG. 6, a support 77 is utilized to support bearing 79 (which receives shaft 40). Bearing 79 has an upwardly extending arm 81 with a pin 82 mounted thereon. Pin 82 has a roller 83 mounted thereon, and roller 83 rolls along the upper portion of wall section 72. A lower frame support 85 is also provided and has an upstanding roller 86 mounted thereon to engage the lower edge of wall 55.

The curvature of gear racks 54 and 74 on frame 18, in conjunction with yoke 46 which is pivotally mounted on frame 18, allows table 20 to be maintained at a low table height, relative to floor level, and yet allows the table to be lengthwise angularly displaced, or tilted, up to 90° in either direction from horizontal.

While not a part of the positioning system to lengthwise angularly displace the frame (and hence the table), the imaging apparatus also includes structure for raising the table (and lowering the same from a raised position) while maintaining the table widthwise horizontal (i.e., not rotated about a lengthwise axis), as well as structure to move the C-arm lengthwise and widthwise with respect to the table and angularly around the table.

As shown in FIG. 1, arms 88 and 89 extend from the opposite outer sides near the top of frame 18 to table 20. As shown, each of these arms has inner and outer portions 91 and 92 with arm portion 92 being pivotally mounted with respect to arm portion 91 just rearwardly of table 20 by means of a pivot pin 94. Table 20 is, in turn pivotally mounted at the other end of arm portion 92 by means of pivot pin 95. Pivoting of the outer arm portions, as well as pivoting of the table itself, is effected by use of pivoting arrangement 97, as shown in FIG. 6. As shown, support 98, mounted on wall 99 extending outwardly from wall 55, has gear 101 mounted thereon, which gear engages straight rack 102. Rack 102 is connected with arm 103 having a cable pulley (not shown) mounted thereon, which cable pulley is part of a pulley and cable arrangement to cause pivotal movement of the outer arm portion 92 with the table being pivoted as needed to maintain the table in a horizontal position as the table is raised or lowered, as needed or desired, by movement of the outer arm portions.

C-arm 21 is mounted on frame 18 for longitudinal movement along the top of the frame (and hence along the length of table 20) in reciprocal directions, as needed or desired, by means of trolley 105. As shown in FIG. 1, trolley 105 is mounted at the top 106 of frame 18 with trolley 105 having rollers 108 and 109 at the rear wall 110 of the trolley riding on opposite sides of inwardly directed horizontal plate 111, rollers 112 and 113 at the front wall 114 of the trolley riding on opposite sides of inwardly directed horizontal plate 115, and rollers 116 and 117 extending downwardly from trolley bottom plate 118 with the rollers contacting the opposite sides of wall 55 at the top thereof. Movement of trolley 105 is effected by pulley and cable arrangement 120, as indicated in FIG. 6. As shown, pulley 121 is mounted on plate 122 (connected to plate 114 of trolley 105) with plate 122 (and trolley 105) being driven by cables 123 extending around pulleys 121 (and other pulleys (not shown) extending along the unit). Rollers 124 and 125 are mounted on plate 122 and roll along walls 55 and 115, respectively.

A counterweight 126 is provided at the forward side of wall 55 (behind front wall 128 as shown in FIG. 1) and is mounted thereat on plate 130 (connected with plate 122). Plate 130 has rollers 132 and 133 thereon, which rollers roll along rail 134 mounted on wall 55. Counterweight 126 is driven in reciprocal directions lengthwise along frame 18 to balance trolley displacement from the center of frame 18 by means of pulley and cable arrangement 120.

As also shown in FIGS. 1 and 2, boom 136 extends forwardly from trolley 105 to C-arm 21 and rearwardly to control unit 138. Boom 136 is moveable forwardly and rearwardly with respect to trolley 105 by means of a rack and gear arrangement (not shown) similar to that shown in connection with pivotal movement of the outer arm portions and table 20 as brought out hereinabove. This movement effects widthwise movement with respect to table 20.

C-arm 21 is also moveable in both clockwise and counter-clockwise directions with respect to the curvature of the C-arm (and hence around table 20), as well as movement in reciprocal twisting directions with respect to the C-arm, as indicated in FIG. 1. Such movements are effected by pulley and cable arrangements and gear and rack arrangements similar to those described hereinabove.

Figure 12:
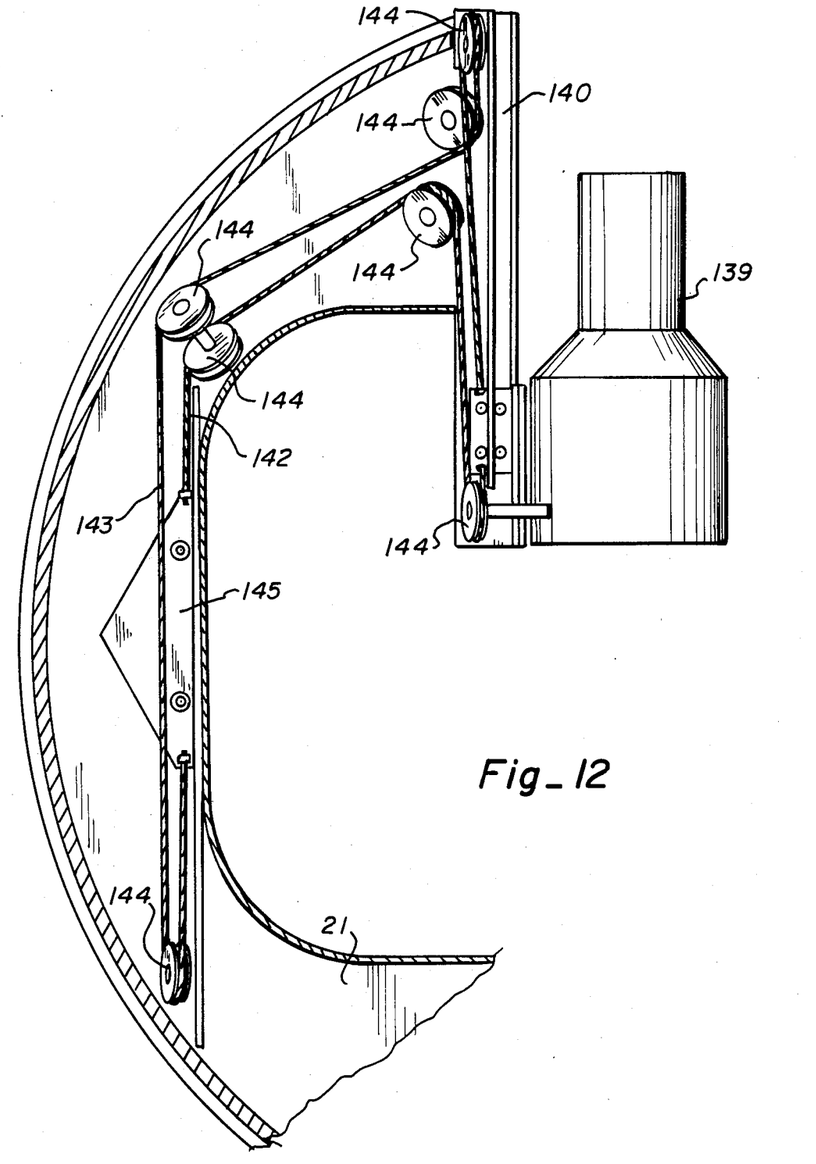
FIG. 12 is a partial perspective and schematic view illustrating a pulley and cable system utilized in conjunction with raising and lowering the radiographic apparatus.

A radiographic instrument, as indicated in FIG. 1, has one portion 139 moveably positioned with respect to plate 140 at the top end of C-arm 21 and another portion 141 in fixed position at the bottom end of C-arm 21. The radiographic instrument can be, for example, X-ray equipment, and movement of portion 139 toward and away from table 20 is accomplished by means of a pulley and cable arrangement 142, as shown in FIG. 12. As shown, cable 143 is connected with various pulleys 144 (one of which is mounted on portion 139 of the radiographic instrument) and with counterweight 145 to counter balance the weight of portion 139 of the diagnostic equipment.

Figure 13:
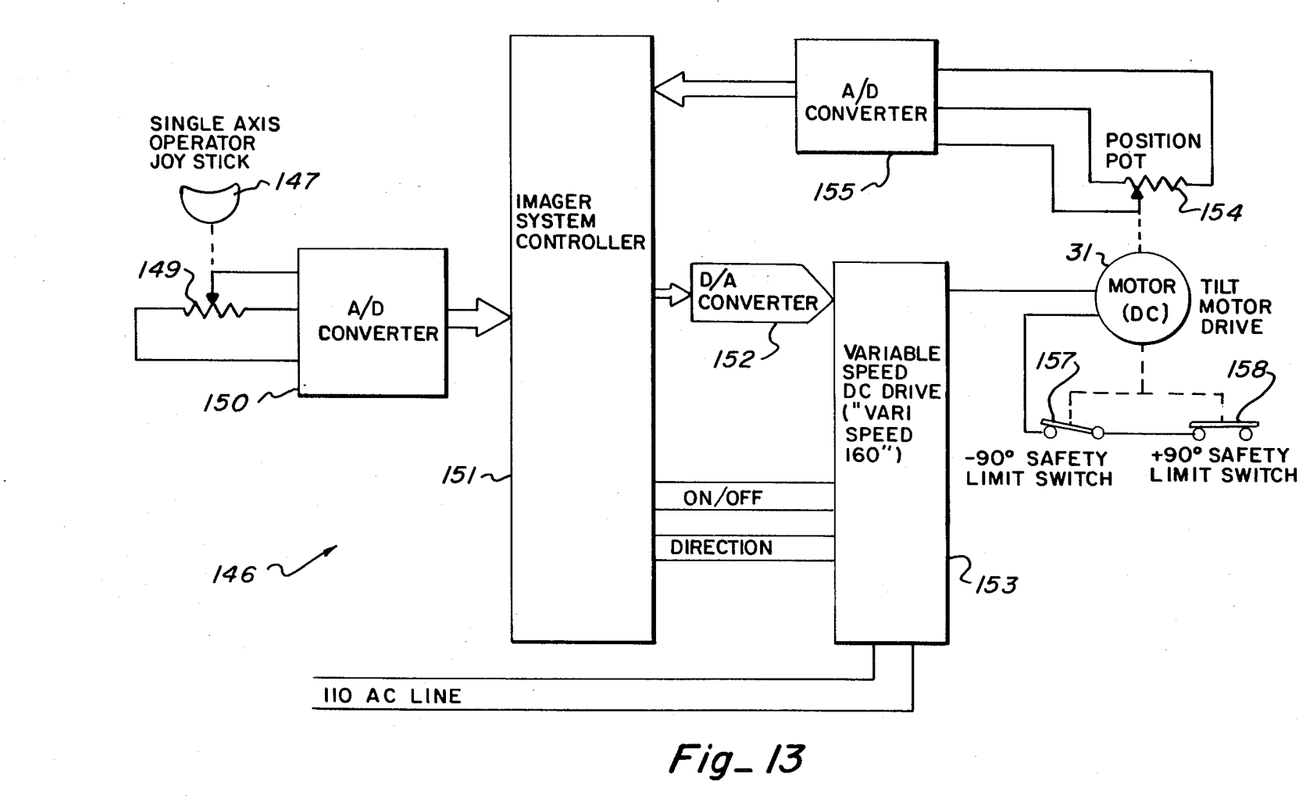
FIG. 13 is a block diagram of an electrical unit which can be utilized for effecting lengthwise angular frame movement.

While the lengthwise angular movement of frame 18 (and hence table 20) may be effected by manually controlling energization of electric motor 31, such movement may also be effected by an electronic control unit 146, as shown in FIG. 13. As shown, movement of joystick 147 is translated into an electrical signal by potentiometer 149, and this analog signal is converted into a digital signal by A/D converter 150 and then coupled to imager system controller 151. The output from controller 151 is converted to an analog output at D/A converter 152 and the resulting analog signal is coupled to a variable speed DC drive 153, the output of which drives motor 31 to cause the desired lengthwise angular movement of frame 18 and, therefore, table 20.

A position potentiometer 154 senses the actual table position and produces an analog output signal indicative thereof, which analog signal is coupled to A/D converter 155 where the signal is converted to a digital signal, which digital signal is then coupled to imager system controller 151. Limit switches 157 and 158 are also provided as safety limits to limit angular movement of the table to a 90° displacement in either direction.

Frame 18 is shown in horizontal position in FIG. 3. In this position, table 20 is also in a horizontal position with no angular displacement about a widthwise central axis. When lengthwise angular displacement is desired (i.e., movement parallel with the lengthwise, or longitudinal, axis), motor 31 is energized (either manually, as by closing a switch connecting the motor to a power source, or by utilizing the system as shown in FIG. 13), and energization of the motor causes gears 41 and 47 to impart driving motion to gear racks 74 and 54, respectively, to cause angular movement of frame 18. As can be appreciated from the foregoing, smooth translating and continuous motion is imparted to frame 18 since a single continuous drive motor is utilized to drive continuous curved gear racks in conjunction with a yoke that is pivoted on frame 18 and has one gear drive mounted thereon. As indicated in FIG. 4, when frame 18 (and hence table 20) is horizontally positioned, yoke 46 is vertically positioned and gears 41 and 47 are at the center of gear racks 74 and 54, respectively. When frame 18 is angularly displaced, yoke 46 pivots about pivot 68 as the frame moves due to movement of gear racks 74 and 54 under the drive force of driving gears 41 and 47 to thereby impart translating movement to frame 18 to move the frame outwardly and upwardly, as shown in FIG. 4, where the frame is shown to be angularly displaced at an angle of about 35° from horizontal. When frame 18 is angularly displaced to a 90° position from horizontal (i.e., to a vertical position as shown in FIG. 5), yoke 46 has pivoted so that the normally lower base portion is now above frame 18 and gears 41 and 47 are near one end of gear racks 74 and 54, respectively.

This lengthwise angular movement of frame 18 allows table 20 to be positioned at a low table height above floor level when horizontally positioned and yet allows the table to be lengthwise angularly displaced to the full vertical position in either direction from horizontal without the then lower end of the table (or frame) contacting the floor (or base) though being constantly adjacent thereto. This enables a focal spot coverage of up to about 70 inches lengthwise of a patient which has not been heretofore possible.

The imaging device is useful for various diagnostic and treatment procedures including, for example, those possible with conventional X-ray equipment, and the positioning system of this invention has been found useful in positioning a patient on the table to aid in successful completion of such procedures.

As can be appreciated from the foregoing, this invention provides an improved positioning system for effecting lengthwise angular displacement of a frame and table that is particularly useful in positioning a patient for imaging by radiographic equipment.

What is claimed is:

1. A system for positioning a table relative to a base, said system comprising actuating means connected with said base and including frame means having said table mounted thereon, said actuating means also including gear means connected with a drive mechanism and gear rack means mounted on said frame means and engaging said gear means, said gear rack means including a first gear rack having a first curvature and a second gear rack having a second curvature that is opposite to that of said first curvature, and said gear means including a first gear engagable with said first gear rack and a second gear engagable with said second gear rack so that said table is angularly displaceable in at least one direction from a horizontal position and with said actuating means causing displacement of said table by imparting a smooth translating motion to said table throughout said displacement.

2. The system of claim 1 wherein said table is used to position a patient for imaging by radiographic equipment.

3. The system of claim 1 wherein said table has a length that is greater than the width, and wherein said angular displacement effected by said actuating means is lengthwise angular displacement of said table.

4. The system of claim 1 wherein said first gear rack is semi-cylindrical in shape and extends along said frame member a distance less than that of said second gear rack, with said second gear rack being other than semi-cylindrical in shape.

5. The system of claim 4 wherein said second gear rack has a curvature at the opposite end portions greater than that of said central portion.

6. The system of claim 1 wherein said drive mechanism is an electric motor.

7. The system of claim 1 wherein said table is positioned by said actuating means to enable substantially full coverage of a patient being imaged on said table by radiographic equipment.

8. A system for positioning a table used with radiographic equipment, said system comprising:
  base means having having drive means mounted thereon;
  frame means having said table mounted thereon, said frame means being a lengthwise elongated member having first and second oppositely curved portions centrally mounted on one side thereof, said first and second curved portions being gear racks;
  translating means having a pair of spaced pivots with one of said pivots being mounted on said base means and the other of said pivots being mounted on said frame means; and
  drive imparting means connected with said drive means and said first and second curved portions of said frame means, said drive imparting means including first and second driving gears each of which engages a different one of said gear racks for imparting drive to said frame meand to cause said frame means to be angularly displaced along the lengthwise axis of said frame means with said translating means causing said angular displacement of said frame means to be along said lengthwise axis of said frame means 9. The system of claim 8 wherein said frame means is mounted on said base means to cause said table to be at a low level to enhance use thereof with radiographic equipment.

10. The system of claim 9 wherein said base means has a floor engaging section and a support section, with said drive imparting means being connected with said support section, and with said translating means and said drive imparting means maintaining said table and frame means close to but out of contact with said floor engaging section during said translating angular displacement.

11. A system for positioning a table used with radiographic equipment, said system comprising:
  base means having drive means mounted thereon;
  frame means having said table mounted thereon, said frame means having first and second oppositely curved portions;
  translating means including a yoke having a pair of spaced pivots mounted on opposite ends thereof with one of said pivots being mounted on said base means and the other of said pivots being mounted on said frame means; and
  drive imparting means connected with said drive means and said first and second curved portions of said frame means for imparting drive to said frame means to cause said frame means to be angularly displaced along a predetermined axis of said frame means with said translating means causing said frame means to be translated along said predetermined axis during said angular displacement.

12. The system of claim 8 wherein said drive imparting means includes an electric motor and energization control means for said electric motor.

13. The system of claim 12 wherein said motor energization control means includes a control unit connected with said motor through a variable speed drive, an actuator connected with said control unit for requesting frame movement, and determining means connected with said motor and said control unit for indicating movement of said frame means.

14. A system for positioning a table used to image a patient on said table by means of radiographic equipment, said system comprising:
  base means having a horizontally extending floor engaging section and a vertical support section;
  frame means having a lengthwise elongated portion at least equal in length to said table with said table being mounted thereon, said frame means having a first curved gear rack on one side thereof with the ends of said first gear rack being below the central portion thereof when said frame means is in a horizontal position, and said frame means having a second curved gear rack on said one side of said frame means with the ends of said second gear rack being above said central portions thereof and said central portion of said second gear rack being adjacent to and below said first gear rack when said frame means is in a horizontal position;
  yoke means having first and second end portions with said first end portion being pivotally mounted on said vertical support section of said base means and said second end portion being pivotally mounted on said frame means at said one side thereof between said first and second gear racks;
  drive means mounted on said base means; and
  first and second drive gears mounted on said base means and driven by said driving means with said driving gears engaging different ones of said first and second gear racks whereby when driven said frame means is caused to be lengthwise angularly displaced and translated in a smooth and continuous motion with said frame means being maintained throughout close to but out of contact with said floor engaging section of said base means.

15. The system of claim 14 wherein said first gear rack has a uniform curvature, and wherein said second gear rack has a non-uniform curvature with the curvature at the opposite ends being greater than that of the central portion.

16. The system of claim 14 wherein said first and second gears are driven along said first and second gear racks in the same lengthwise direction during lengthwise angular displacement of said frame means.

17. The system of claim 14 wherein said driving means includes an electric motor and reduction means with said electric motor driving one of said first and second gears through said reduction means.

* * * * *